(12) United States Patent
Keelapang et al.

(10) Patent No.: US 7,722,885 B2
(45) Date of Patent: May 25, 2010

(54) DENGUE VIRUS MUTANT STRAIN MBU 01-2002

(75) Inventors: Poonsook Keelapang, Amphur Muang (TH); Nopporn Sittisombut, Amphur Muang (TH); Watchara Kasinrerk, Amphur Muang (TH); Prida Malasit, Bangplad (TH)

(73) Assignee: National Science and Technology Development Agency, Klong Luang, Phathumthani (TH)

( * ) Notice: Subject to any disclaimer, the term of this patent is extended or adjusted under 35 U.S.C. 154(b) by 1948 days.

(21) Appl. No.: 10/626,585

(22) Filed: Jul. 25, 2003

(65) Prior Publication Data

US 2009/0004721 A1    Jan. 1, 2009

(30) Foreign Application Priority Data

Jul. 26, 2002    (TH) ...................................... 075425

(51) Int. Cl.
*A61K 39/12*    (2006.01)

(52) U.S. Cl. ................. 424/218.1; 435/69.1; 435/235.1
(58) Field of Classification Search ....................... None
See application file for complete search history.

(56) References Cited

U.S. PATENT DOCUMENTS 6,372,221 B2 *    4/2002    Mannhalter et al. .... 424/196.11

* cited by examiner

*Primary Examiner*—Stacy B Chen

(57) ABSTRACT

The invention includes a genetic construct and a mutant dengue virus, designated as strain MBU 01-2002, which is a mutant dengue virus generated by genetic modification of the 13-amino acid sequence just proximal to the pr-M junction within the prM coding region of the genome. The modification involves increasing the number of positively charged amino acids and abolishing the negatively charged amino acids in this pr-M junction sequence. The mutant dengue virus strain MBU 01-2002 possesses less prM protein on the viral envelope than the prototype dengue virus, is capable of inducing infected C6/36 cells to fuse at neutral pH, is as efficient as the prototype virus in the intracellular multiplication, but is defective in its release from infected cells.

5 Claims, No Drawings

SEQUENCE LISTING

<160> NUMBER OF SEQ ID NOS: 3

<210> SEQ ID NO 1
<211> LENGTH: 39
<212> TYPE: DNA
<213> ORGANISM: Dengue virus
<220> FEATURE:
<221> NAME/KEY: mutation
<222> LOCATION: (1)..(39)

<400> SEQUENCE: 1
cggtgcacgc ggaccaggca ttccaagaga tctaggaga          39

<210> SEQ ID NO 2
<211> LENGTH: 43
<212> TYPE: DNA
<213> ORGANISM: Artificial Sequence
<220> FEATURE:
<223> OTHER INFORMATION: Primer

<400> SEQUENCE: 2
tatggacggt gcacgcggac caggcattcc aagagatcta gga          43

<210> SEQ ID NO 3
<211> LENGTH: 45
<212> TYPE: DNA
<213> ORGANISM: Artificial Sequence
<220> FEATURE:
<223> OTHER INFORMATION: Primer

<400> SEQUENCE: 3
gatctcctag atctcttgga atgcctggtc cgcgtgctcc gtcca          45

DENGUE VIRUS MUTANT STRAIN MBU 01-2002

CROSS-REFERENCE TO RELATED APPLICATIONS

This application claims priority to That Application No. 075425 filed Jul. 26, 2002.

FIELD OF THE INVENTION

The present invention relates to dengue virus containing a full genome-length dengue virus genome with a defined mutation.

BACKGROUND OF THE INVENTION

Dengue virus is a causative agent of dengue fever and dengue hemorrhagic fever, which are widespread in several tropical countries around the world. Transmission of dengue virus among humans occurred through mosquito biting activity; infected human serve principally as the reservoirs for transmission in the urban setting. Among viral isolates obtained from infected humans and mosquitoes, four serologically defined types (serotypes) of dengue virus are known, all of which can cause potentially fatal dengue hemorrhagic fever (D.S. Burke and T. P. Monath (2001) Flaviviruses, P. 1043-1125, in D. M. Knipe, P. M. Howley, D. E. Griffin, R. A. Lamb, M. A. Martin, B. Roizman and S. E. Strauss (ed.), Fields Virology, 4$^{th}$ ed. Lippincott Williams & Wilkins, Philadelphia, Pa.). In human, primary infection by dengue virus of any serotype generally causes milder diseases and induces immunity only against the infecting serotype. As cross protective immunity is short-lived, secondary infection by other dengue serotypes is common in countries where two or more serotypes co-circulate. It is well accepted that secondary infection increases the risk of developing dengue hemorrhagic fever. Effective prevention of dengue hemorrhagic fever will require a vaccine, which can induce protective immunity against all four serotypes of dengue virus.

Dengue virus is a member of the Genus Flavivirus in the Family Flaviviridae. The virion is spherical in shape with the diameter of about 50 nm. The outer part of the virion (envelope) consists of lipid bilayer and two different glycoproteins, E and prM/M (B. D. Lindenbach and C. M. Rice. (2001) p. 991-1041 in D. M. Knipe, P. M. Howley, D. E. Griffin, R. A. Lamb, M. A. Martin, B. Roizman and S. E. Strauss (ed.), Fields Virology, 4$^{th}$ ed. Lippincott Williams & Wilkins, Philadelphia, Pa.). The core is composed of another protein, C, in association with the single-stranded RNA genome. In each virion, one molecule of about 10.7 kb long RNA genome is present; it encodes three structural proteins and seven non-structural proteins, which are required for virus multiplication inside the infected cells, but are not components of virion. The organization of the genome is as follows: 5' cap-5' untranslated region-C-prM/M-E-NS-NS2A-NS2B-NS3-NS4A-NS4B-NS5-3' untranslated region-3' end. This genome organization is common to all flaviviruses.

Following the assembly of virion in the endoplasmic reticulum, the envelope of immature virions, consisting of only prM and E proteins, is further modified by glycosylating enzymes in the Golgi apparatus and by the proteolytic enzyme, furin, in the trans-Golgi network. Specifically, when immature virion is exported along the secretory pathway to the extracellular milieu, furin cleaves the protein prM internally at the pr-M junction, generating virion-associated M protein and soluble pr peptide, which no longer associate with the virion (K. Stadler, et al. (1997) J. Virol. 71:8475-8481). Cleavage of prM is absolutely necessary for the ability of the mature, extracellular virion of flavivirus to initiate productive infection of the host cell (S. Elshuber, et al. (2003) J. Gen. Virol. 84:183-191). However, cleavage of prM can be incomplete and extracellular virions of several flaviviruses were known to contain varying amount of prM protein. The significance of the remaining prM on the envelope is not yet known.

Recent structural data of the immature particles of dengue virus reveal that the prM proteins associate with the E proteins as sets of prM-E heterodimer (Y. Zhang, et al. (2003) EMBO J. 22:2604-13). The prM proteins project out of the surface whereas the E proteins lie flat and parallel to the lipid bilayer of the envelope. The protruding portion of the prM proteins covers the tip of the E protein that is responsible for fusing activity of E protein. The structure of a preparation of the mature dengue virion in which all prM proteins are cut is quite different from the immature virion including the formation of E-E homodimers (R. J. JKuhn, et al. (2002) Cell, 108:717-25), indicating that cleavage of prM by furin leads to a significant rearrangement of the envelope proteins. Such rearrangement must be important for generating infectious viral particles.

It has been repeatedly observed that the extracellular virions of dengue virus usually contain remaining prM protein on their envelope (R. Anderson, et al. (1997) J. Virol. 71: 4226-4232; R. T. He, et al.(1995) J. Med. Virol. 45: 451-461; E. A. Henchal et al. (1985) Am. J. Trop. Med. Hyg. 34: 162-169; J. M. Murray et al. (1993) J. Gen. Virol. 74: 175-182; V. B. Randolph et al. (1990) Virology 174: 450-458; J. T. Roehrig et al. (1998) Jamaica. Virology 246: 317-328; S. Wang et al. (1999) J. Virol. 73: 2547-2551). The observations were made in dengue virus prepared from a number of cell lines of both mosquito and mammalian origins in several laboratories. These dengue virus preparations are infectious and able to generate new rounds of infection efficiently.

When compared with other flaviviruses in which the prM protein is completely cleaved, an incomplete cleavage of prM in dengue virus coincides with a lower number of positively charged amino acids and also the presence of two negatively charged amino acids within the 13-amino acid, pr-M junction proximal sequence, which extends beyond the P6 and P4 boundary previously known to affect cleavage of target protein by furin (G. Thomas (2002) Nat. Rev. Mol. Cell. Biol. 3: 753-766; K. Nakayama (1997) Biochem. J. 327: 625-635; A. Zhou et al. (1999) J. Biol. Chem. 274: 20745-20748). Thus, one of the distinctive features of dengue virus is the conservation of the pr-M cleavage junction sequence, which allows only partial cleavage by host cell-derived furin. Alterations of dengue pr-M cleavage junction may modify the structural characteristics of the virion and the biology of dengue virus, especially the replication kinetics in ways that are not yet known. Alterations of this pr-M junction sequence in dengue virus can take a number of ways, including: a substitution of each amino acid position to alter one at a time the charge characteristics and the size of the R group; substitution of two or more amino acid positions in various combinations, a deletion of one or more charged amino acid positions; an insertion of one or more charged amino acids or any combination of these manipulation methods. Depending on the nature of the amino acid changes and the property of furin in specific cell lines tested, the cleavage of prM protein in the mutant dengue viruses can either be enhanced, lowered, or unaffected. Alteration of the cleavage of the N-terminal of prM protein of a related flavivirus, yellow fever virus, has been known to reduce virus replication by affecting the production of virus within the infected cells (E. Lee et al. (2000) *J. Virol.* 74: 24-32).

BRIEF SUMMARY OF THE INVENTION

The present invention is a genetic construct and a dengue virus containing a full genome-length dengue virus genome with a defined mutation within the 13-amino acid-coding region proximal to the pr-M cleavage junction. The mutation involves increasing the number of positively charged amino acid and abolishing the negatively charged amino acid of the pr-M cleavage junction, which results in an enhanced cleavage of the prM protein to the M protein. The mutant dengue virus possesses less prM protein on the viral envelope than the prototype dengue virus. The mutant dengue virus was able to bind, enter and replicate inside the infected cells as efficiently as the prototype dengue virus, but was ineffective in its release from infected cells into the extracellular compartment, causing a greatly reduced virus titer and replication kinetics. The mutant dengue virus strain MBU01-2002 may be useful as an immunogen for the generation of protective immunity against dengue virus infection or dengue hemorrhagic fever in human in the future.

BRIEF DESCRIPTION OF THE SEVERAL VIEWS OF THE DRAWING

Not Applicable

BRIEF DESCRIPTION OF SOME OF THE SEQUENCES IN THE SEQUENCE LISTING

SEQ ID NO: 1 is a 13-mer of Dengue virus mutant strain MBU 01-2002.

SEQ ID NO: 2 is primer which can be used to introduce specific mutant sequence into the pr-M junction of dengue genome (sense primer: 5' TATGGACGGTGCACGCGGAC-CAGGCATTCCAAGAGATCTAGGA 3').

SEQ ID NO: 3 is primer which can be used to introduce specific mutant sequence into the pr-M junction of dengue genome (anti-sense primer: 5' GATCTCCTAGATCTCTTG-GAATGCCTGGTCCGCGTGCTCCGTCCA 3').

DETAILED DESCRIPTION OF THE INVENTION

1. Generation of a Mutant Dengue Virus Strain MBU 01-2002

Dengue virus mutant strain MBU 01-2002 was generated by altering a specific gene segment of a virulent dengue serotype 2 virus strain 16681, also called prototype dengue virus. The virus strain 16681, a wild type strain, was isolated from a Thai patient with dengue hemorrhagic fever. A change was introduced specifically at the pr-M junction, just proximal to the cleavage site of a host proteolytic enzyme (furin), within the coding region for the prM protein. The alteration was performed in successive steps, as follows:

A plasmid subclone containing the sequence nt 1-1547 of a full-length cDNA clone of dengue 2 virus strain 16681 (R. Sriburi et al. (2001) *J. Virol. Methods* 92:71-82) was altered by introducing substitution mutation at two nucleotide positions, 666 (T666A mutation) and 709 (A709G mutation), using a PCR-based, site-directed mutagenesis scheme. The alteration resulted in new restriction enzyme recognition sites for Nde I and BamH I at the nucleotide positions 666 and 709 of the viral sequence, respectively. The presence of the new recognition sites was confirmed by nucleotide sequence analysis of the resultant plasmid subclones.

In order to introduce specific mutant sequence into the pr-M junction of dengue genome, two single-stranded oligonucleotides, SEQ ID NO: 2 (sense primer: 5' TATGGACG-GTGCACGCGGACCAGGCATTCCAAGAGATCTAGGA 3') and SEQ ID NO: 3 (anti-sense primer: 5' GATCTCCTA-GATCTCTTGGAATGCCTGGTCCGCGTGCTCCGTCCA 3'), were designed and synthesized.

The oligonucleotides were mixed and allowed to anneal at 37° C. to generate a short double-stranded oligonucleotide with a Nde I-compatible end and a BamH I-compatible end. The annealed, double-stranded oligonucleotide was then ligated into the plasmid subclone mentioned above, which was previously digested with Nde I and BamH I enzyme and was devoid of a short Nde I-BamH I fragment. Following transformation of the ligated product into *E. coli* and the selection with ampicillin, the presence of mutant sequence in the resultant subclones was confirmed by nucleotide sequence analysis. The mutant pr-M junction sequence was then introduced into the plasmids containing the 5' half-genome (nt positions 1-4497) and subsequently the full-length cDNA clone (nt positions 1-10723). The final full-length cDNA plasmid contained the intended mutant sequence at the pr-M junction, which encodes a mutant prM protein with the following amino acid changes (numbering is according to the sequence of the polyprotein of dengue virus serotype 2 as described in R. M. Kinney et al. (1997) *Virology* 230: 300-308):

The amino acid position 193: from threonine to arginine.
The amino acid position 196: from threonine to arginine.
The amino acid position 197: from methionine to threonine.
The amino acid position 198: from glycine to arginine.
The amino acid position 199: from glutamic acid to histidine.
The amino acid position 200: from histidine to serine.
The amino acid position 201: from arginine to lysine.
The amino acid position 203: from glutamic acid to serine.
The amino acid position 204: from lysine to arginine.

The full genome-length cDNA plasmid clone with mutant pr-M junction sequence was linearized by digesting the 3' end of viral sequence with Xba I. The linearized plasmid was employed as the template for the generation of capped, full-length RNA using SP6 RNA polymerase in the presence of cap analog (4 mM) and RNA precursors. The in vitro transcription reaction was allowed to proceed at 30° C. for 4 hours.

The in vitro RNA transcript was then purified, quantitated and transfected into a mosquito cell line, C6/36, with the use of a cationic lipid reagent, lipofectin. Following transfection, C6/36 cells were maintained at 29° C. in the presence of Leibovitz's L15 medium supplemented with 3% fetal bovine serum and 10% tryptose phosphate broth (R. Sriburi et al. (2001) *J. Virol. Methods* 92:71-82). Mutant dengue virus liberated from transfected C6/36 cells into culture medium was detected by focus immunoassay using the PS pig fibroblast cell line as early as day 2 after transfection and reached a high level on day 7 after transfection. Mutant virus was harvested from the culture, mixed with fetal bovine serum to the final concentration of 20% and stored at −70° C.

The appropriate conditions for amplifying the mutant dengue virus in vitro are as follows: an adherent C6/36 cell line was infected with mutant virus at the ratio of 1-10 infectious virions per 100 C6/36 cells in the volume of 1-2 ml at room temperature. After 2 hours of incubation, culture medium (Leibovitz's L15 medium supplemented with 3% fetal bovine serum and 10% tryptose phosphate broth) was added to 15 ml and the cell line was maintained at 29° C. and the liberated virus was monitored daily. When high virus level was reached, the mutant virus was harvested, mixed with fetal bovine serum to the concentration of 20% and stored in small aliquots at −70° C.

2. Properties of the Mutant Dengue Virus Strain MBU 01-2002

The mutant dengue virus strain MBU 01-2002 is 10-1,000 folds less efficient in the replication in vitro than the prototype dengue virus strain 16681 when tested in the C6/36 mosquito cell line, PS pig fibroblast cell line, Vero monkey kidney cell line and human embryonic kidney 293T cell line.

The extracellular virions of the mutant dengue virus strain MBU 01-2002 contain less prM protein on the viral envelope than the prototype dengue virus strain 16681 when tested by immunoblot analysis of unlabelled virions, and by SDS-PAGE analysis of specifically immunoprecipitated, $S^{35}$-labelled virions. Reduced level of prM on virion envelope indicates higher efficiency of the cleavage of pr-M junction during virus export through the trans-Golgi network of infected cells. By design, the remaining prM protein on the envelope of the mutant dengue virus strain MBU01-2002 contains a higher number of positively-charged amino acids than those of the prototype dengue virus strain 16681.

The mutant dengue virus strain MBU 01-2002 is capable of inducing infected C6/36 mosquito cell line to fuse at both neutral condition (pH=7.0) and acidic condition (pH less than 7.0) whereas the parent 16681 dengue virus requires acidic condition. Induction of infected cell fusion by the mutant dengue virus strain MBU 01-2002 occurs well at 29° C., but is less efficient at 40° C.

The mutant dengue virus strain MBU 01-2002 binds and enters PS cell line and 293T cell line as efficiently as the prototype dengue virus strain 16681. Within the infected cells, the mutant dengue virus strain MBU 01-2002 replicates as efficiently as the prototype dengue virus strain 16681, but was exported out of the infected cells to a lesser extent than the prototype dengue virus.

The invention provides a significant and unexpected improvement to the art of mutant dengue virus production. One with skill in the art could expect that a mutant dengue virus with enhanced cleavage of the prM protein to be more (or, at least, as) efficient in the replication in cultured cell lines as the prototype virus. However, unexpectedly, the present invention identifies a mutant dengue virus with defective release out of the infected cells, causing the lower virus titer and lower growth kinetics in cultured cell lines. The mutant dengue virus also differs from the prototype dengue virus in its ability to induce infected mosquito cell fusion at neutral pH upon incubation at 29° C. Because of its lowered replication kinetics, the invention has a potential to serve as a live, attenuated vaccine candidate for inducing protective immune response against dengue virus in humans.

We claim:

1. A recombinant genetic construct encoding a dengue viral genome comprising a full-length genome of a dengue virus wherein the construct is modified at a 13-amino acid encoding region just proximal to the pr-M cleavage site so that it is devoid of negatively-charged amino acids and contains additional positively-charged amino acids relative to a wild-type dengue virus, wherein the modification results in enhanced internal cleavage of the prM protein relative to the wild-type dengue virus.

2. The genetic construct of claim 1 wherein said genetic construct comprises DNA.

3. A mutant dengue virus comprising a full-length genome of a dengue virus wherein the virus comprises a 13-amino acid-encoding region just proximal to the pr-M cleavage site which is devoid of negatively-charged amino acids and contains additional positively-charged amino acids relative to a wild type dengue virus, wherein the mutant virus contains less prM protein on its viral envelope than the wild type dengue virus due to an enhanced internal cleavage of the prM protein.

4. A mutant dengue virus of claim 3 wherein the virus induces infected C6/36 mosquito cell line to fuse at a neutral pH to a greater extent than a wild type dengue virus.

5. A mutant dengue virus of claim 4 wherein the virus is exported out of the infected cells to a lesser extent than a wild type dengue virus, resulting in a lower virus titer in a culture medium.

* * * * *